(12) United States Patent
Jung et al.

(10) Patent No.: US 10,299,667 B2
(45) Date of Patent: May 28, 2019

(54) MOVEMENT DEVICE AS WELL AS SYSTEM FOR CLEANING MEDICAL INSTRUMENTS

(71) Applicant: BANDELIN Patent GmbH & Co. KG, Berlin (DE)

(72) Inventors: Rainer Jung, Berlin (DE); Juliane Helke, Berlin (DE); Jonas Möhricke, Berlin (DE); Claudia Häsen, Oberkrämer (DE); Ferdinand Biermann, Berlin (DE); Sören Hoppenau, Berlin (DE)

(73) Assignee: BANDELIN patent GmbH & Co. KG, Berlin (DE)

( * ) Notice: Subject to any disclaimer, the term of this patent is extended or adjusted under 35 U.S.C. 154(b) by 162 days.

(21) Appl. No.: 15/350,845

(22) Filed: Nov. 14, 2016

(65) Prior Publication Data

US 2017/0135565 A1    May 18, 2017

(30) Foreign Application Priority Data

Nov. 13, 2015    (DE) .................... 20 2015 106 167 U

(51) Int. Cl.
*A61B 1/12*        (2006.01)
*B08B 3/12*        (2006.01)
(Continued)

(52) U.S. Cl.
CPC .............. *A61B 1/123* (2013.01); *A61B 34/30* (2016.02); *A61B 90/70* (2016.02); *B08B 3/12* (2013.01);
(Continued)

(58) Field of Classification Search
CPC ...... A61B 1/123; A61B 2090/701; B08B 3/12
See application file for complete search history.

(56) References Cited

U.S. PATENT DOCUMENTS 4,278,101 A * 7/1981 Tanaka .................. A61B 1/123
                                                134/167 C
4,281,674 A * 8/1981 Tanaka .................. A61B 1/123
                                                134/170
(Continued)

FOREIGN PATENT DOCUMENTS

DE    202006020523 U1    2/2009
DE    102013019382 A1    5/2015
(Continued)

OTHER PUBLICATIONS

Extended European Search Report issued in European Application No. 16198744.1 dated Jun. 29, 2017; 9pp.
(Continued)

*Primary Examiner* — Michael E Barr
*Assistant Examiner* — Benjamin L Osterhout
(74) *Attorney, Agent, or Firm* — Studebaker & Brackett PC

(57) ABSTRACT

A movement device and systems for cleaning medical instruments. The movement device includes an adapter for coupling at least one medical instrument. The adapter includes at least one coupling element which is movable by way of a drive, wherein the coupling element is designed such that on coupling the medical appliance, at least a region of the medical appliance can be brought into movement by way of moving the coupling element, wherein force transmission between the drive and the coupling element is effected in a contact-free manner.

11 Claims, 14 Drawing Sheets

(51) Int. Cl.
*A61B 34/30* (2016.01)
*A61B 90/70* (2016.01)
*A61B 17/00* (2006.01)

(52) U.S. Cl.
CPC ............... *A61B 2017/00876* (2013.01); *A61B 2090/701* (2016.02)

(56) References Cited

U.S. PATENT DOCUMENTS

| | | | |
|---|---|---|---|
| 2006/0100501 A1* | 5/2006 | Berkelman | A61B 17/3403 600/415 |
| 2007/0107755 A1* | 5/2007 | Noguchi | A61L 2/18 134/94.1 |
| 2007/0169799 A1* | 7/2007 | Noguchi | A61B 1/00057 134/56 R |
| 2007/0234494 A1* | 10/2007 | Suzuki | A61B 1/122 15/104.2 |
| 2007/0234495 A1* | 10/2007 | Suzuki | A61B 1/122 15/104.095 |
| 2009/0044845 A1* | 2/2009 | Cui | A61B 1/123 134/56 R |
| 2009/0217956 A1 | 9/2009 | Noguchi et al. | |
| 2011/0315173 A1 | 12/2011 | Pfaffinger et al. | |
| 2013/0312793 A1* | 11/2013 | Ionidis | A61B 19/34 134/22.19 |
| 2013/0333125 A1* | 12/2013 | Majeed | A61B 1/123 15/21.1 |
| 2015/0251224 A1* | 9/2015 | Dawson | B08B 3/04 134/23 |

FOREIGN PATENT DOCUMENTS

| | | |
|---|---|---|
| EP | 2837353 A1 | 2/2015 |
| WO | 20120148266 A1 | 11/2012 |
| WO | 20150020906 A1 | 2/2015 |
| WO | WO 2015020906 A1 * | 2/2015 ............. A61B 34/30 |

OTHER PUBLICATIONS

German Search Report issued in German Application No. DE 20 2015 106 167.6 dated Nov. 9, 2016; 3pp.

* cited by examiner

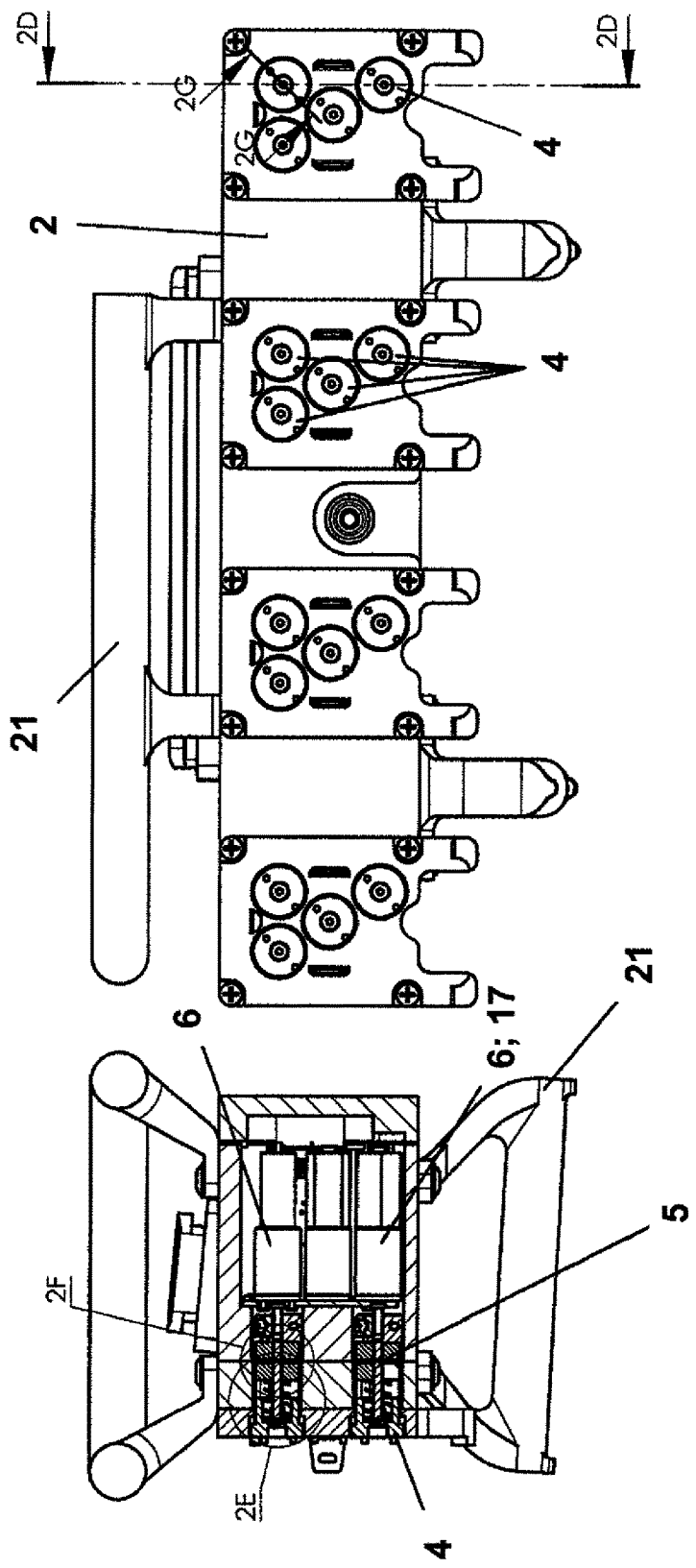

(detail according to Figure 2D)

(detail according to Figure 2D)

(section 2G-2G according to Figure 2C)

Figure 3A:
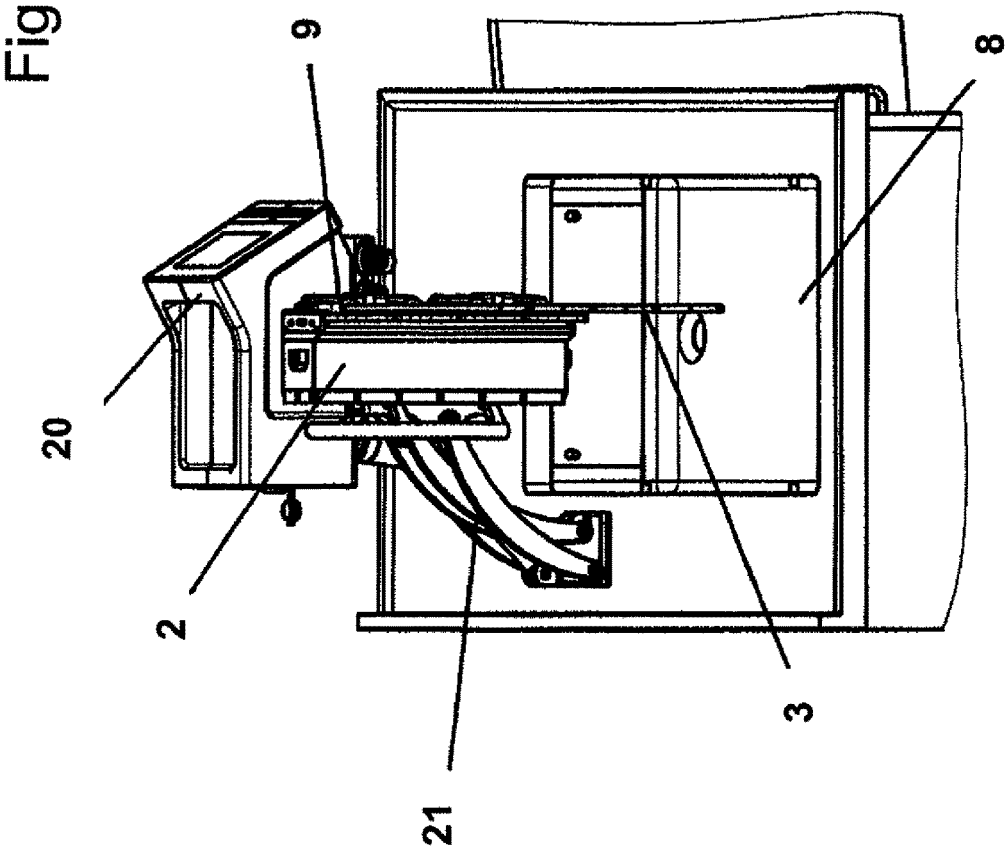
Figure 3B:
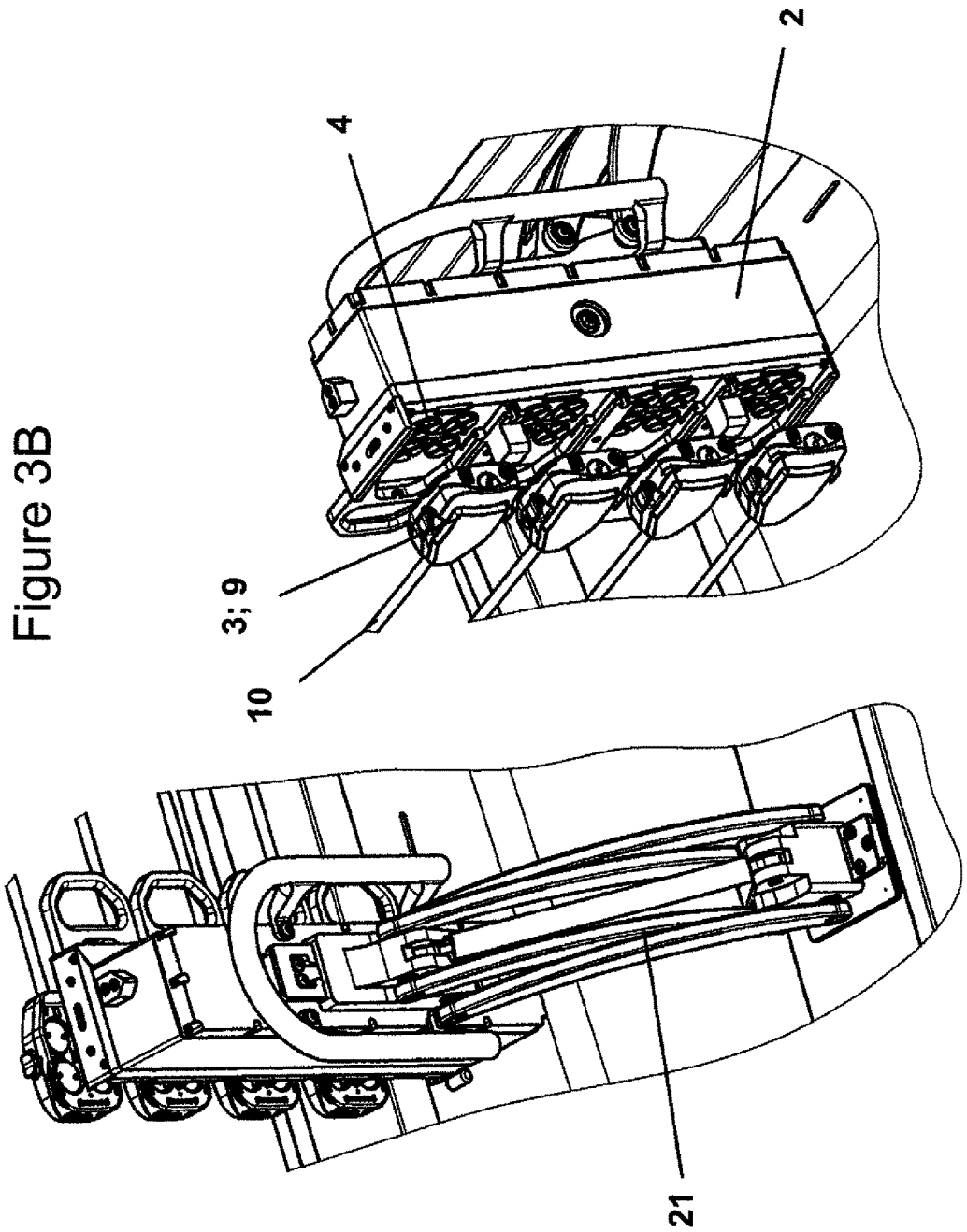
Figure 3C:
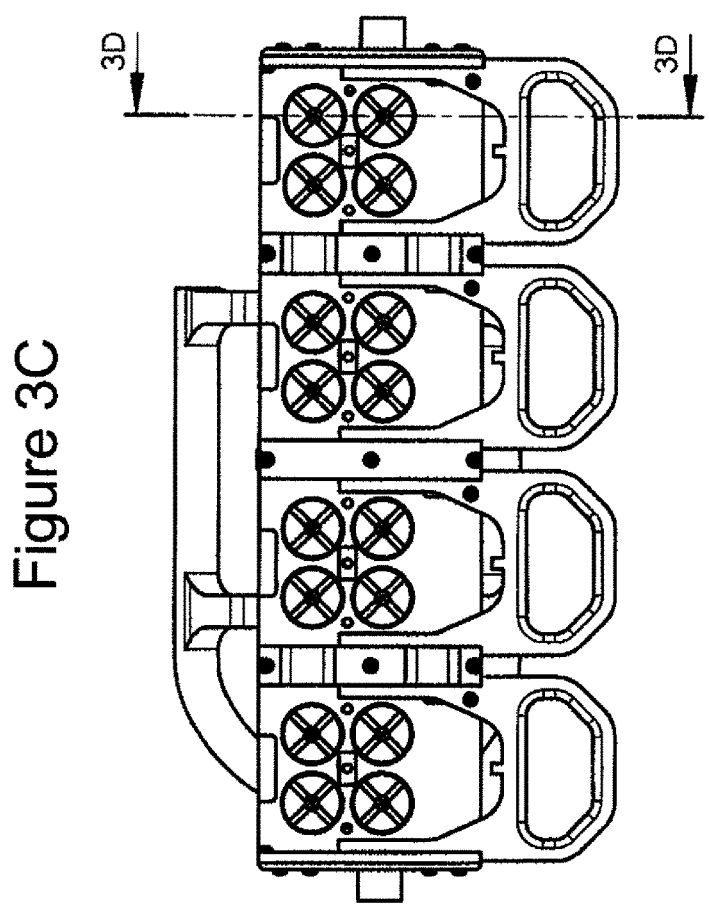

(section 3D-3D according to Figure 3C)

21

Figure 4A:
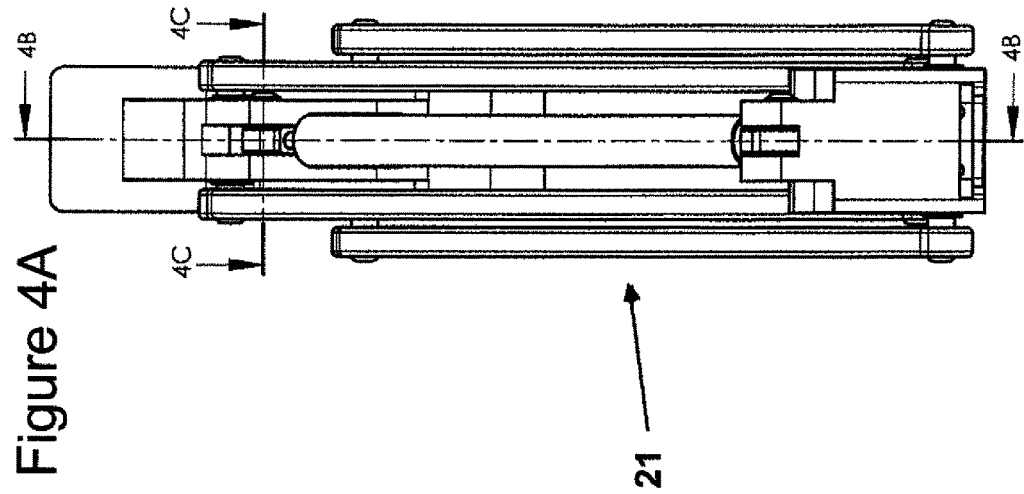

(section 4B-4B according to Figure 4A)

(section 4C-4C according to Figure 4A)

Figure 4B:
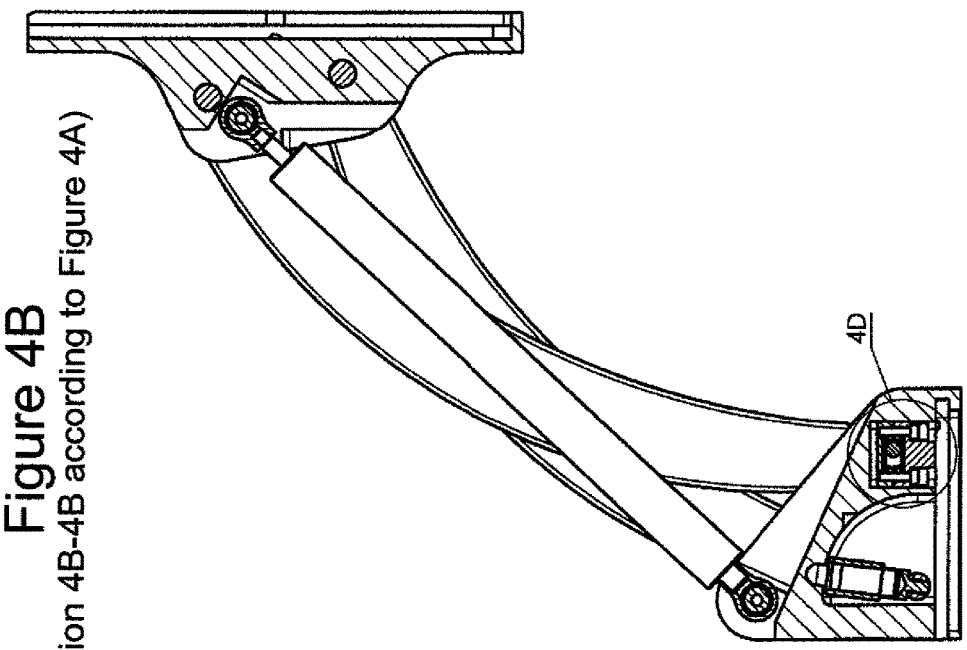

(detail according to Figure 4B)

Figure 5A
Figure 5B
(section 5B-5B according to Figure 5A)
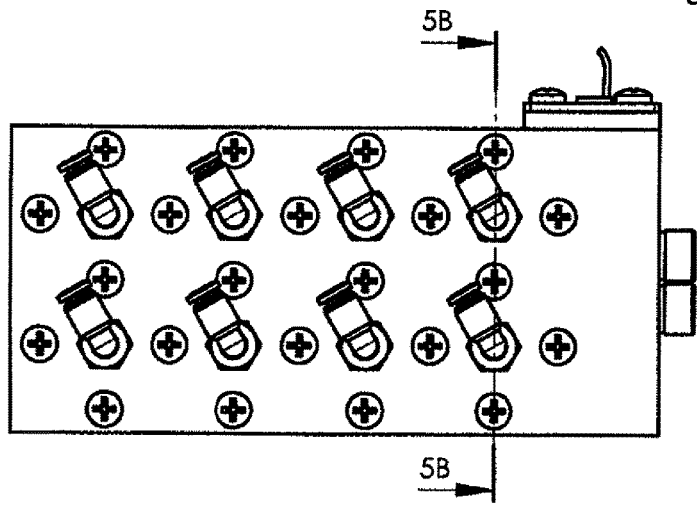
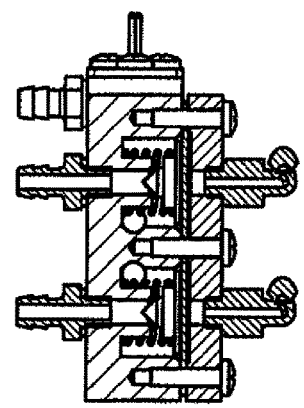
Figure 5C
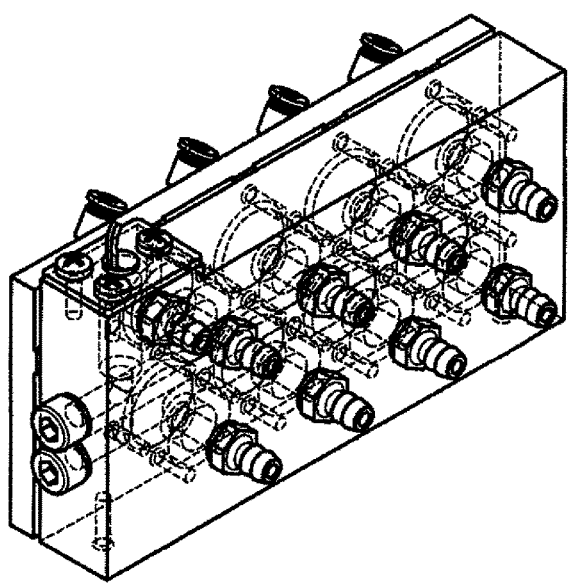

MOVEMENT DEVICE AS WELL AS SYSTEM FOR CLEANING MEDICAL INSTRUMENTS

This application claims benefit of priority to German Patent Application 20 2015 106 167.6 filed Nov. 13, 2015, the entire content of which is incorporated herein by reference.

The present protective right relates to a movement device, as well as to a system for cleaning medical instruments. In a particular manner, this is suitable as an additional device for an ultrasound cleaning appliance.

On cleaning medical instruments by way of low-frequency ultrasound, foreign particles on or in medical instruments are detached on account of specific mechanisms effected by ultrasound (such as cavitation, micro-streaming, jet formation, etc).

Here, in particular, surgical instruments are placed in a basket and are subsequently brought into a trough of an ultrasound cleaning appliance which is filled with a liquid. The trough is subsequently subjected to ultrasound, so that the foreign particles and adhesions can detach within a short period of time. Optionally, this process is assisted by way of the addition of suitable cleaning and/or disinfectant preparations, which are added to the liquid.

A further application is known from the field of laparoscopy. Here, foreign particles can occur not just at the outer side of the instrument, but also in a lumen of an instrument shank of the instrument. In order to develop a cleaning effect here, it is known for example to connect the distal end of the shank onto an adapter which allows fluid to be drawn from the proximal to the distal end of the shank, so that apart from the rinsing effect occurring due to this, the effect of the ultrasound can also be utilised for cleaning within the shank lumen. Particularly in the case of more complex medical appliances, such as endoscopic medical appliances for example, which have several degrees of freedom, cleaning is very important in order to avoid infections during subsequent operations on humans or animals. First and foremost, it is important for all moving parts to be cleaned and disinfected.

In view of this, the task of providing a movement device or a system for cleaning medical instruments arises, wherein this system on the one hand should also be able to be simply operated by an untrained person and on the other hand permits a very thorough cleaning of medical instruments.

This object is achieved by the subject-matters of the independent claims. This firstly relates to a movement device, comprising an adapter for coupling at least one medical instrument, wherein the adapter comprises at least one coupling element which is movable by way of a drive, wherein the coupling element is designed such that on coupling the medical appliance, at least one region of the medical appliance is brought into movement by way of the movement of the coupling element, wherein the force transmission between the drive and the coupling element is effected in a contact-free manner.

Due to the movement of the coupling element and the movement of the moving parts of the medical instrument, said latter movement being caused by this, this medical instrument is cleaned "under movement", so that all adhering particles can be removed and a subsequent disinfection is effected. In particular, here it is not necessary to attach parts of the drive input or drive output below the liquid surface of the ultrasound bath, in particular due to the contact-free force transmission. This permits for example a best possible alignment of the medical appliances to the walls of the ultrasound bath which emit ultrasound.

It is particularly advantageous to attach this movement device within an ultrasound bath, and for a control to not only permit the control of movement of the medical instruments, but also of the ultrasound intensity and of a rinsing (pressure rinsing and/or suction rinsing) of the instrument shank. Moreover, in particular, the contact-free force transmission permits a kinematic decoupling of individual degrees of freedom, with the movement of the medical instruments. It is thus possible to call up a precisely defined program for cleaning specific medical instruments, with which program each movement degree of freedom of the medical instrument can be modeled. A very clearly reproducible and well documentable cleaning which helps to avoid the clinging of the smallest of residues results only from such a procedural manner.

The present protective right moreover relates to a system for cleaning medical instruments, preferably a movement device according to the features specified above (wherein here however a contact-free force transmission is not necessary, and this can also be effected in a mechanically coupled manner). For all these systems (thus contact-free or mechanically coupled, for example by way of belts, cogs etc), it lends itself for the adapter for the coupling of at least one medical instrument to comprise the coupling element movable by way of the drive, wherein the coupling element can be designed such that on coupling the medical instrument, at least one region of the medical instrument can be brought into movement by way of movement of the coupling element, said system furthermore comprising a pivoting and/or lifting device which is designed in a manner such that the adapter can be displaced between:

a) an attachment condition which is arranged above the ultrasound bath or a trough bath, and
b) a cleaning condition, with which the adapter at least regionally is arranged below the water surface, for example of an ultrasound cleaning bath and/or in a spray mist or the like.

In this manner, it is quite simple for medical personnel to attach the medical appliances on the adapter and to then bring them into a cleaning condition, with which these are aligned in the best possible manner, for example aligned onto a spray mist or onto an ultrasound source in a water bath.

Further developments of the device mentioned above are shown hereinafter. It is to be noted that all further developments can also be combined with one another, inasmuch as this is not expressly mentioned as being technically incompatible. In particular, the embodiments of the pivoting and/or lifting device also particularly lend themselves for mechanically force-transmitting as well as contact-free drives of the coupling elements for driving the medical instruments. In particular, all movement devices or systems in the context of this protective right application can be combined with a channel selector which is envisaged for a suction rinsing and/or pressure rinsing device for rinsing at least one lumen of a medical appliance. This is characterised in that it is preferably pneumatically operated, and the moving parts consist for example of plastic. The channel selector (see also the example of FIGS. 5a and 5c) in particular is suitable for complex medical instruments which have several lumens, or for a multitude of corresponding medical instruments. Here, it is also advantageous that small dead volumes can be achieved and that the channel selector is essentially maintenance-free, so that good cleaning results can be achieved also over the longer term. Here, it is to be expressly noted that the applicant reserves a separate protection for this channel selector according to the sentences above or the figures, for example by way of a divisional application.

One embodiment of the movement device for medical instruments envisages the at least one coupling element being designed in a rotatable manner. Hereby, this can be coupled onto a complementary part of the medical instrument to be cleaned, and here, a mechanical coupling between the part of the medical instrument to be driven as well as the coupling element is created by way of a positive fit.

It also lends itself to provide several coupling elements in one adapter. This for example can be of a nature such that four medical instruments are envisaged for coupling onto an adapter, wherein each of the medical instruments is assigned to four coupling elements in each case. In this manner, medical instruments with several degrees of freedom can also be moved in a complete manner (i.e. in all degrees of freedom) and preferably additionally yet through-rinsed, in order to achieve a best-possible cleaning effect.

One embodiment envisages the contact-free force transmission device being designed as a magnetic coupling. This for example can be a permanent-magnetic, contact-free magnetic coupling, as are known for example with magnetic agitators for laboratory needs. However, "contact-free" within the scope of the present protective right is to be understood as all contact-free magnetic or electromagnetic or inductive methods. The only thing which is important here is that a drive element and a driven element are separated from one another through a separating wall or pasts a gap with a certain distance, in order in particular to achieve a fluid sealing.

Preferably, the drive and the coupling element are separated from one another by a fluid-tight separating layer for this. This can be for example a plastic wall and/or a plastic membrane. Separating layers which are easy to clean and do not interfere with the magnetic flux are provided in this manner.

As already mentioned above, the movement device is preferably arranged in a bath which can be subjected to ultrasound. A very good cleaning effect can be achieved in this manner, due to the fact that apart from the movement of the instruments in a water bath, the ultrasound is yet also used for additional cleaning. As a rule, in a trough-like bath, on whose for example outer side ultrasound generators are attached, this is effected by way of an ultrasound field being applied onto a fluid in the trough bath, and the movement device with its adapter arranging the medical instruments such that these medical instruments at least in regions are below a fluid surface of the trough bath.

Apart from this embodiment, the movement device according to the protective right however can also be placed for example in a water jet or in a water spray mist, in order to thus also achieve a movement of the medical instrument under the influence of fluid.

The medical instruments which are provided here for cleaning are preferably endoscopic instruments. These for example are endoscopic instruments with a coupling part for coupling onto the adapter, with an instrument shank connecting onto the coupling part and with an operation part which is attached on the end of the instrument shank which away from the coupling part. Concerning these instruments, it is particularly important to carry out a cleaning, not only in the region of the operation part, but also within the instrument shank, since infectious material can collect here if the cleaning is not adequate, and this can endanger patient safety over the longer term.

These endoscopic instruments often comprise several operation parts which are movable independently of one another and which are movable independently of one another by different coupling elements.

The independent movement of individual coupling elements is one aspect, for which the applicant reserves the claim for separate protection and would like to follow this up in a possible later divisional application or subsequent application. For this, the following aspects are also of interest:

Each pivot of a robotic instrument (of an endoscopic instrument, see above) is driven by a suitable actuator/motor, in order to ensure a complete and gentle movement of the robotic instruments (endoscopic instruments) and to rule out any overloading. Each actuator is [closed-loop] controlled by a microprocessor which monitors the torque of the actuator. The control loop for example only includes the driven side of the actuator on account of the control variable (for example current of the actuator). The magnetic coupling and its influence on the friction and movement form should preferably be determined by way of a comparison method. The torque which is required for the complete and reliable movement of the instruments, plus the parasitic torques, result from the friction, and should be provided and controlled by the actuator and microprocessor (thus the control unit) respectively. The parasitic influences at each driven pivot are possibly different due to tolerances in the manufacture of the movement device.

For this, it is possible to calibrate each driven pivot after the assembly. The actuator drives the pivot without workload, for example for 10 to 100 seconds, e.g. 60 seconds, whilst the motor current of the actuator is continuously measured. The determined values are then utilised as an initial value of the motor current for the movement. The torque at the coupling element/on the robotic instruments which is required for the complete and reliable movement is added to the initial value for each pivot. A torque loading which always remains the same thus results for each driven instrument pivot. In the software, for example, there is a maximal value for the permitted torque defining the limit of the non-positive fit of the magnetic coupling, so as to counter an overload. Moreover, a mechanical protection against overload of the instruments is also given, since the magnetic coupling only permits a torque transmission up to a certain limit torque, and slips beyond this.

Within the scope of the present protective right or possible divisional applications, it is thus not only possible to provide a torque limitation electronically, but also by way of the strength of the magnetic coupling, for example by way of the selection of the strength or number of corresponding permanent-magnetic elements, in the force transmission.

The calibration possibilities described above, in particular are conceived for a contact-free force transmission. This can be implemented mechanically in different ways. Thus one embodiment envisages a drive-side part of the force transmission comprising a rotatable drive element which preferably at least in regions comprises permanent-magnetic material and which is preferably axially displaceable with respect to other parts of the drive. It is constantly pulled onto the separating layer (membrane) by way of this, for example by the magnets on the counter side, and variances in the magnetic transmission force and friction are reduced by way of this.

A further embodiment envisages a driven-side part of the force transmission being provided, in which part the coupling element is resiliently mounted. The rotation angle of the corresponding counter piece on the medical instrument is initially of no importance with such a resiliently mounted coupling element/dog part, and it is firstly pressed down on inserting the dog part and then locks in at a later stage on rotation (see for example FIG. 2E).

A further embodiment, at the driven-side part of the force transmission, envisages a compression spring being arranged between the coupling element and a rotatable driven element, wherein the movement element at least in regions comprises permanent-magnetic material. It is therefore not necessary to design the coupling element itself in a magnetic manner. The torque is applied in a separate part (which is connected to permanent magnets), and the coupling element is connected to this by a spring.

A further development envisages a drive-side part and a driven-side part of the force transmission device in each case comprising at least one region of permanent-magnetic material, wherein the parts are related to one another such that the rotation of the drive-side part entails a rotation of the driven-side part. Hereby, a different number or different quantity of magnetic material can be provided on both sides. For example, it is possible to provide individual permanent magnets in an oppositely lying manner in the form of a revolver. A good centering is firstly achieved by way of this and the torque (slip moment) of the magnetic coupling can furthermore be set by way of the selection of the number or quantity which is to say strength of the magnetic material.

As described above, it is also possible for one motor to be provided per coupling element in each case. With this, it is possible to set an independent movement and free programming of the movement course as well as of slip torques etc.

A further development envisages a suction rinsing and/or pressure rinsing device being provided for rinsing at least one lumen of the medical appliance. A rinsing of the instrument shank is achieved by way of this, supplementary to the mechanical movement. Hereby, it is also possible to achieve a rinsing in both directions, in order to be able to clean in a particularly efficient manner, in particular with undercuts.

A control unit can hereby also be provided, and this not only controls the drive of the coupling element and thus of the medical instrument, but also the rinsing device or also the subjection to infrasound. A very individual program for individual medical instruments can be called up and documented in this manner, so that the best possible cleaning can be achieved here, and documented.

A further development envisages different adapters being able to be integrated into the movement device and also being exchangeable amongst one another. By way of this, it is ensured that medical instruments of a different construction type or of different manufacturers can be cleaned in a single movement device. The total costs for the cleaning are reduced by way of this. A pivoting and/or lifting device can be combined with all of the movement devices mentioned above. This device preferably has kinematics which apart from the lowering and lifting also achieves a rotation. On account of this, it is possible on the one hand to attach onto the adapters in a condition which is favourable for the user, and on the other hand, in a cleaning condition, to arrange the medical instruments in the best possible manner in the water bath or the water bath subjected to ultrasound. Here, it is particularly advantageous for the attachment (equipping) to be effected by the medical personnel in such a way that considered from a standing operating person, a frontal coupling of the medical instruments onto the adapter is possible, and that overhead work is not necessary here. For the cleaning condition, it is particularly advantageous if this is aligned such that the best possible subjection to ultrasound can be effected, i.e. no interfering baskets or mounts lie between the wall of the ultrasound bath and the medical instrument.

Further developments are mentioned in the special description.

Figure 1:
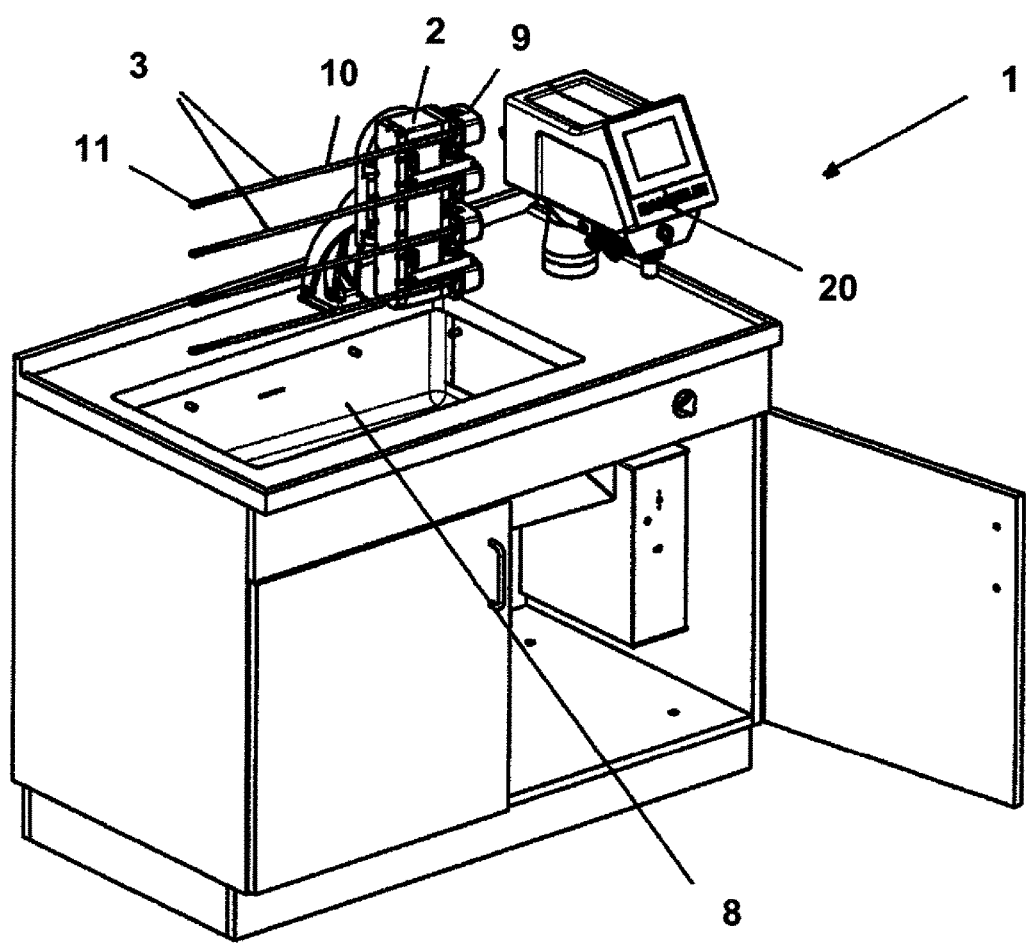
Figure 2A:
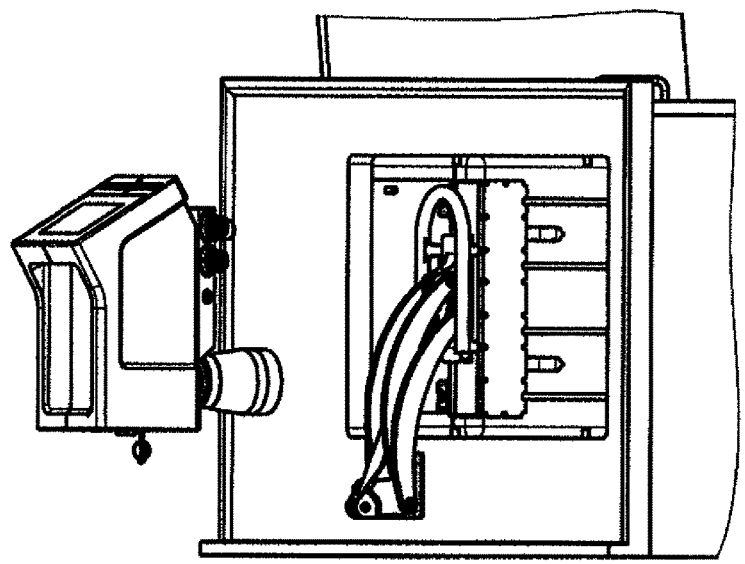
Figure 2A:
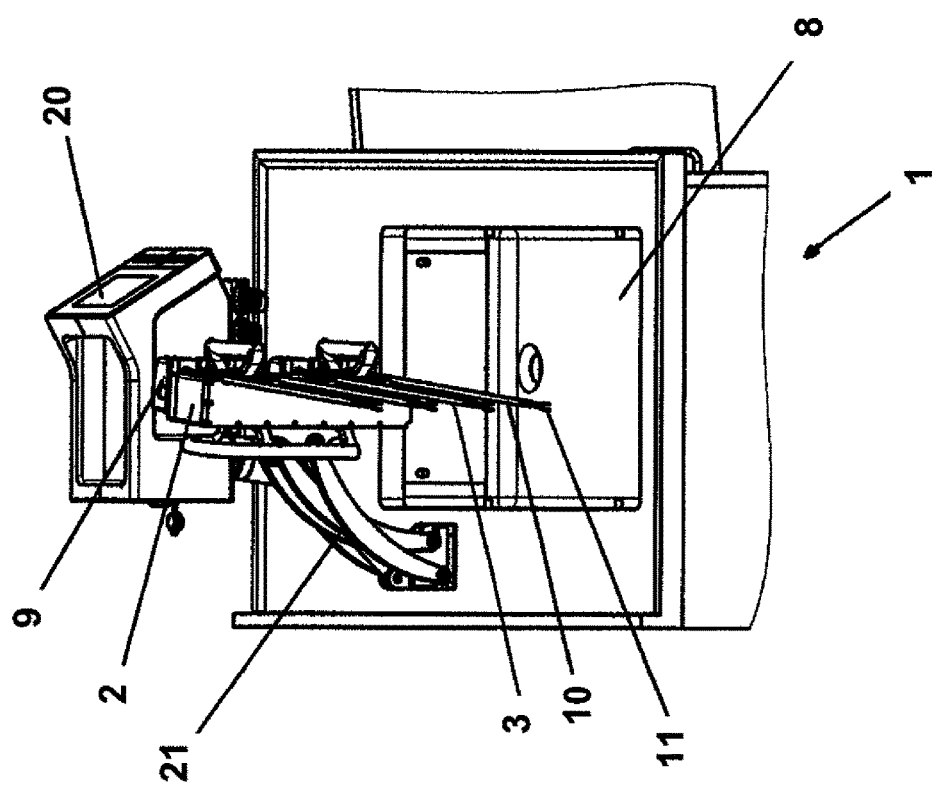
Figure 2B:
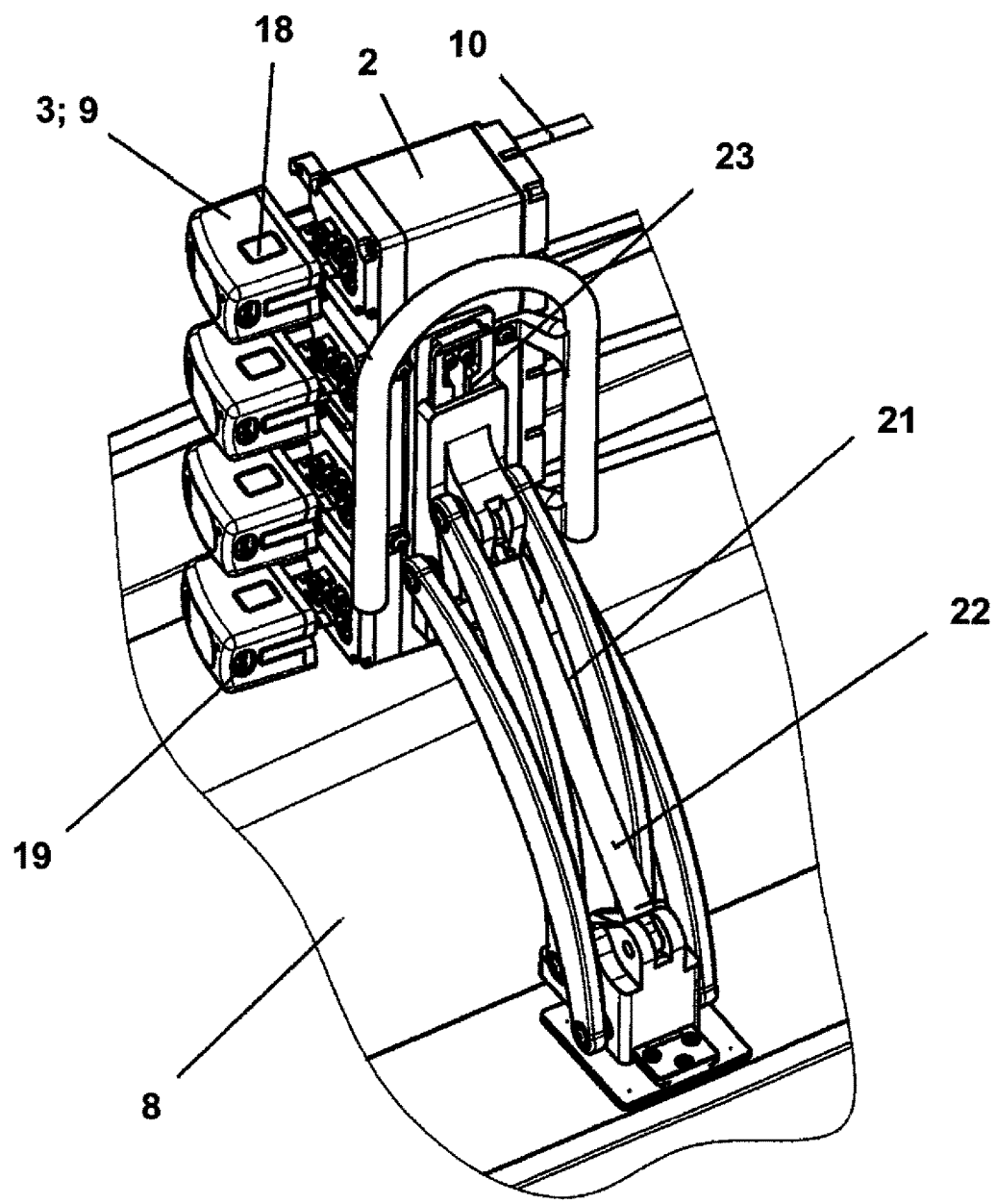
Figure 2F:
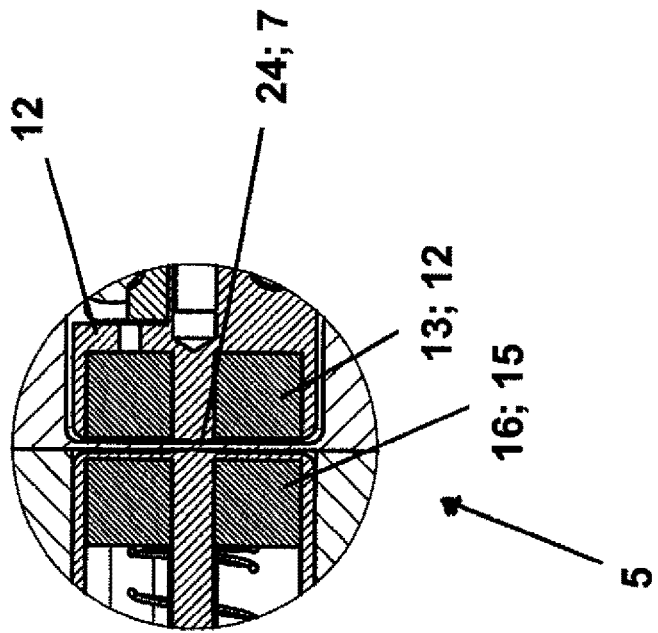
Figure 2E:
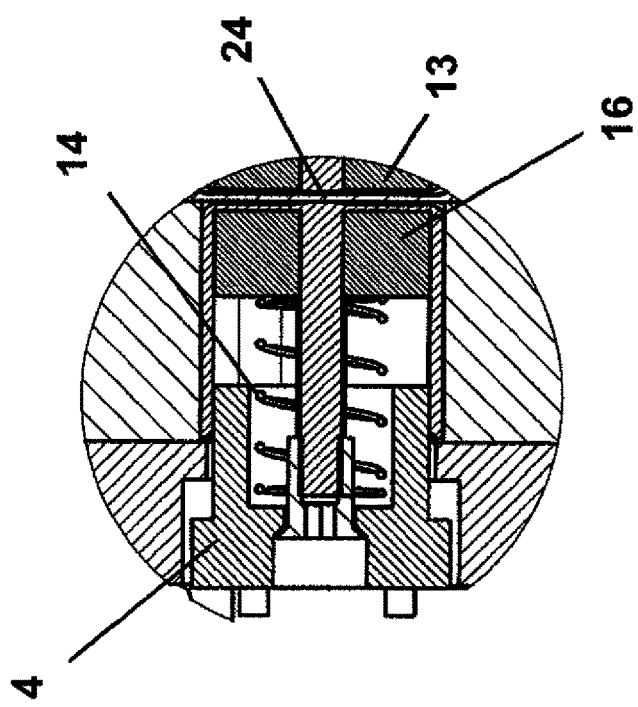
Figure 2G:
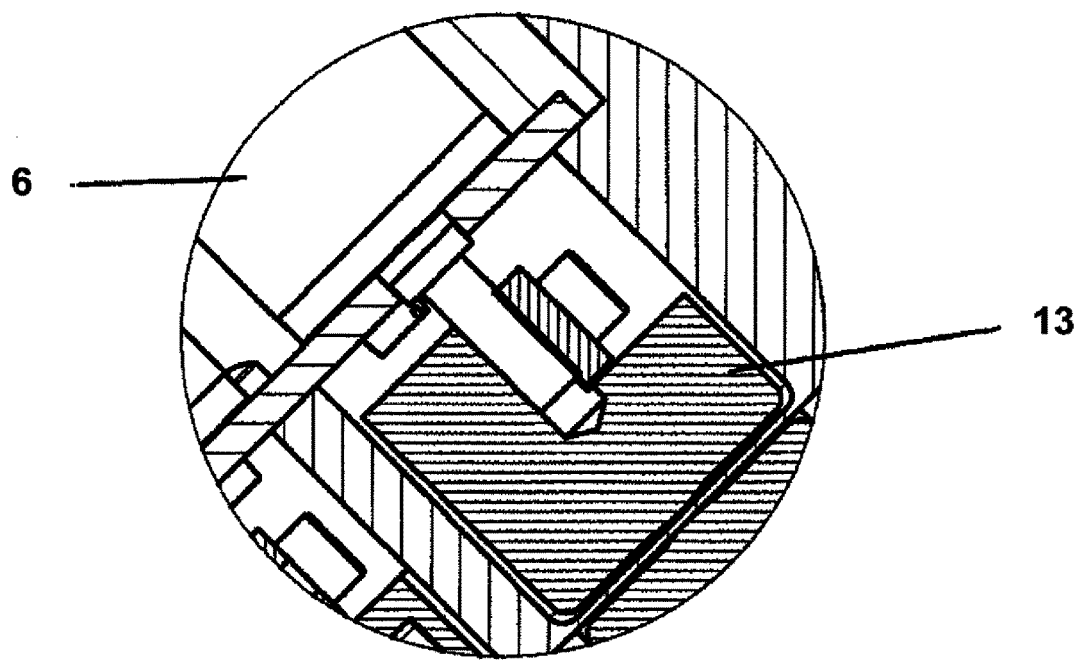
Figure 3D:
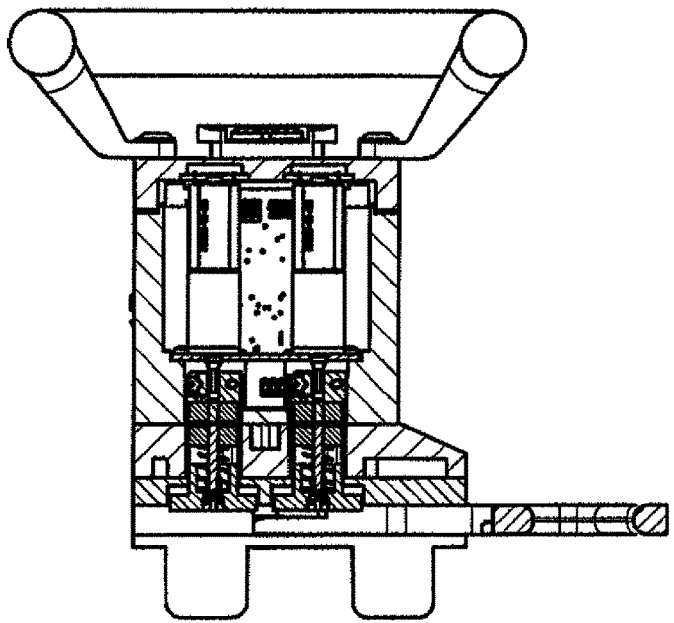

Further details are now explained by way of figures. There are shown in:

FIG. 1 a system for cleaning medical instruments, comprising a movement device for medical instruments, FIG. 2a the system of FIG. 1, in an attachment position for medical instruments (at the left) as well as in the cleaning condition (at the right), FIG. 2b a first embodiment of an adapter of a movement device according to the invention, with medical instruments for cleaning represented suspended in front of this;

FIG. 2c a plan view of an adapter for coupling medical instruments, according to FIG. 2b (now without medical instruments which are represented suspended in front of this), FIG. 2d a section according to 2D-2D according to FIG. 2c, FIG. 2e a detail according to FIG. 2d, FIG. 2f a detail according to FIG. 2d, FIG. 2g a section according to 2G-2G according to FIG. 2c, FIG. 3a a further variant of a system, now with an adapter different than in FIG. 2a, again in the attachment condition (at the left) and in the cleaning condition (at the right), FIG. 3b two views of the adapter/of the movement device according to FIG. 3a, with medical instruments suspended in front of this, FIG. 3c a view of an adapter according to FIG. 3a (without medical instruments suspended in front of this), FIG. 3d a section according to 3D-3D according to FIG. 3c, FIG. 4a a pivoting and/or lifting device for coupling a movement device or an adapter, FIG. 4b a section according to 4B-4B according to FIG. 4a, FIGS. 4c to 4e sections of the pivoting and/or lifting device according to FIG. 4a, FIGS. 4f to 4h three different movement conditions of a system as well as of a moment device, in the lateral view and well as FIGS. 5a to 5c views and sections of a channel selector for use in a pressure and/or suction device for rinsing medical instruments.

FIG. 1 shows a system, comprising a movement device 1, comprising an adapter 2 for coupling at least one medical instrument 3. The adapter 2 comprises at least one coupling element 4 (for this, see FIG. 2b ff or FIG. 3b ff), which is movable by way of a drive, wherein the coupling element is designed such that at least a region of the medical appliance can be brought into movement by way of the movement of the coupling element, on coupling the medical appliance 3. The force transmission between the drive and the coupling element is effected in a contact-free manner, and details concerning this are explained for example in FIGS. 2d to 2g, in which rotatable coupling elements are shown. In all examples, in each case several coupling elements are provided in an adapter and the contact-free force transmission device is designed as a magnetic coupling. This however is not absolutely necessary, and other contact-free methods or different numbers of coupling elements can alternatively also be provided (see introductory description). A control unit 20 is likewise to be seen in FIG. 1. This control unit on the one hand effects the control of the drive of all coupling elements. The control of a rinsing device for suction rinsing and/or pressure rinsing of the medical instrument 3 is moreover ensured by this control device. Finally, an ultrasound device subjecting a water bath 8 to ultrasound is also controlled. For this, oscillation systems for the generation of ultrasound are attached on the outer side of the water bath, for example in the base region and/or on the side walls. The control unit 20 moreover has premanufactured programs for the targeted control of the ultrasound exposure/rinsing/drive. Suitable protocols can moreover be created for the documentation of cleaning procedures, and as the case may be, can be recorded over or stored per data lead.

FIG. 2a at the left side shows a system 1 with an ultrasound bath 8 (not filled with water in this condition) as well as, arranged above this, with a pivoting and/or lifting device with a coupled adapter 2 to which medical instruments 3 are coupled. The medical instruments 3 comprise an instrument shank 10. The coupling parts 9 (see FIG. 2b, mechanisms for moving an operation part 11 at the other end of the instrument shank 10 are attached in these coupling parts) on the one hand connect onto this instrument shank 10. These coupling parts as a rule have several mechanisms which are coupled onto respective coupling parts in order to move the mechanisms and by way of this to easily reach all locations during cleaning (details concerning this can be found further below).

In FIG. 2a, it can be easily seen that the adapter can be fitted with the coupled medical instruments by way of a combined pivoting and lifting movement of the pivoting and/or lifting device 21. With the embodiment which is shown in FIG. 2a on the left, an operating person who stands in front of the system (see FIG. 1) can carry out the equipping of the adapter 2 with medical instruments 3 in a simple manner. The control unit 20 can moreover be easily operated in this position. As soon as the attachment with the medical instruments has been effected, the pivoting and/or lifting device can be brought into the position shown on the right in FIG. 2a.

FIG. 2b shows a further view of the representation of FIG. 2a (left side), with which the medical instruments 3 are represented suspended in front of the adapter 2. By way of this, it is visible that a coupling (thus a fixation, preferably by way of snapping-in) of the coupling parts 9 of the medical instruments 3 onto the adapter 2 is effected. Additionally, a pressure and/or rinsing device which rinses the instrument shank 10 of the medical instrument can be attached on the coupling part, also for rinsing at least one lumen 19.

The pivoting and lifting device shown in FIG. 2b is characterised by stability and good operation. It is possible to lock the device 21 in the extreme positions (i.e. in the cleaning condition (such as in FIG. 2a at the right) or also in the attachment condition (FIG. 2a at the left or FIG. 2b)). A gas compression spring 22 is provided, in order to avoid an unnecessary high speed on pivoting/lifting. The details of the pivoting mechanism are dealt with once again further below. The pivoting and lifting device moreover comprises a U-shaped lever, so that the adapter 2 does not need to be directly gripped by an operating person. Moreover, one can see that the adapter 2 is connectable to the pivoting and lifting device 21 by a detent mechanism 23, in order to be able to couple different adapters in this manner.

FIG. 2c shows a view of the adapter 2 shown in FIG. 2b (without a medical instrument 3 lying in front of it). The U-shaped holding grip of the pivoting and/or lifting mechanism 21 is also to be seen. The adapter of FIG. 2c is suitable for coupling four medical instruments 3. Each of these medical instruments comprises four mechanisms which are movable via suitable coupling elements 4. Each one of these mechanisms ensures a movement at the end of the instrument shank, thus at the operation part 11 of a medical instrument (see FIG. 2a at the left). The control of the individual coupling elements 4 can be effected completely independently of one another by way of the control unit 20. There are therefore no kinematic constrained movements between individual coupling elements, and each coupling element is freely displaceable concerning its movement cycle. Moreover, it is advantageous that a maximum torque can be envisaged individually for each coupling element, either electronically or mechanically, so that damage to the operation part 11 of the medical instrument is ruled out. Of course, it is however also possible to commonly move the coupling elements of an individual medical instrument or also commonly for all individual instruments, by way of a single drive.

FIG. 2d shows a section according to 2D-2D from FIG. 2c. In this section, two coupling elements are shown in section, and these are driven by two drives 6. A force transmission in the form of a magnetic coupling 5 is provided between the drive 6 and the coupling element 4. With regard to the details of this magnetic coupling 5, these are dealt with once again hereinafter.

FIG. 2e shows a resiliently mounted coupling part, and the rotation angle of the respective counter-piece on the mechanism of the coupling part 9 of the medical instrument 3 is thus of no significance, since the dog part is firstly pressed down on inserting the coupling element 9 into the adapter 2, and then latches into the corresponding mechanism of the medical instrument on locking. In FIG. 2e and in detail, it is practically well seen that permanent magnetic material 6 (for example cylinder-shaped magnets) are provided in a corresponding driven part which is driven in rotation by the drive 6 (e.g. the motor 17, see below regarding this). A compression spring 14 which permits an axial displaceability between the coupling element 4 and the part, in which the permanent-magnetic material 16 is accommodated, is also provided. A constrained guidance between these two is radially represented, so that a rotation of the permanent-magnetic material 16 leads to a rotation of the coupling element 4.

FIG. 2f shows a detail according to FIG. 2d. Here, it can be clearly seen that with the magnetic coupling 5, the torque of the motors is transmitted via permanent magnets through a closed membrane, from the water-tight interior of the drive (the electrical parts of the drive 16 in the adapter are thus encapsulated in a water-tight manner) to the outside. According to the detail according to FIG. 2f, the friction on the membrane (e.g. a plastic wall 7 or plastic membrane) is minimised by way of spherical applicators on both magnet parts. Thus what is to be seen is that driving is effected at the right side by the drive 6 by way of permanent magnetic material (permanent magnets 13; see drive element 12) and the drive output is effected at the left side by way of the permanent magnetic material 16 (see driven element 15) being rotated corresponding to the permanent-magnetic material 13.

FIG. 2g shows a further section (see section 2G-2G according to FIG. 2c). Herein, it is shown that the motor shaft of the drive 6 is free in the axial direction. Since the distance to the membrane could vary given a fixed positioning of the motor-side magnetic part (with permanent-magnetic material 13), in this embodiment, a connection of the motor is mechanically given only in the radial direction, and a freedom of movement is provided in the radial direction. By way of this, it is constantly pulled onto the membrane by the magnets on the counter side, and variances in the magnetic transmission force and friction are reduced in this manner.

FIG. 3a shows a further embodiment of a system 1, wherein here the adapter 2 is designed differently. The difference lies in another type of medical instruments 3 being able to be coupled. The difference between FIGS. 2a and 2b in essentially to be seen in that the coupling parts 9 in the cleaning condition (see FIG. 3a, at the right) now point towards the base of the trough, wherein these are essentially oriented to a wall in the embodiment according to FIG. 2a.

This once again becomes clear when considering the details concerning FIGS. 3b to 3d, where the respective description of FIGS. 2a to 2f is referred to for avoiding repetitions.

FIG. 4a now shows a plan view of a pivoting and lifting device 21 according to the invention, with corresponding levers as well as a gas compression spring 22. Here, spring bolts are also provided, so that the pivoting and lifting device at a certain position has a detent position noticeable by the user, and a spring-loaded bolt which at this position latches into a pocket in the counter-piece, is located on a shaft which is connected to the arms of the pivot lever. Details concerning this are shown in the further representations (FIGS. 4b to 4e). A blocking bolt is represented in FIG. 4b, and this has the following function: the pivot and lifting device 21 should not be removable from its receiver if this is not in its uppermost position (attachment condition). For this reason, a bolt is seated on a shaft connected to the arms, in an eccentrically mounted manner. The bolt moves into a corresponding bore and blocks, if a movement into the cleaning condition is effected.

Figure 4C:
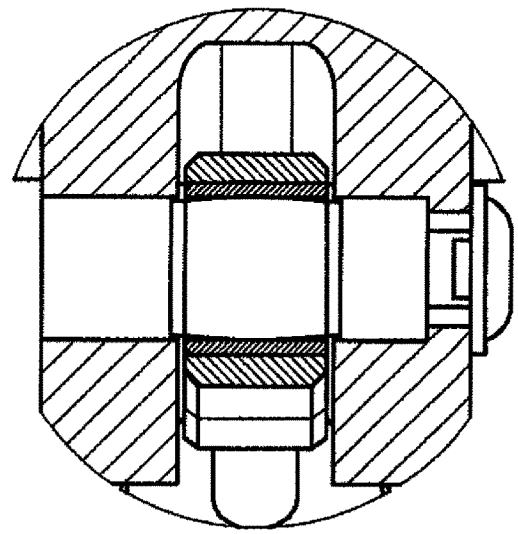

FIG. 4c shows details of a mounting of the gas compression spring (the term gas compression spring also includes so-called "gas-tension springs"; what is important is merely the fact that a resiliency/damping of the movement is possible by way of a compressible material). The gas compression spring, as is to be seen in FIG. 4c, is mounted on a slightly crowned shaft. It cannot therefore be subjected to torsion forces which load it incorrectly and which could lead to leakage, which would result in a drop of the force of the gas compression spring.

FIG. 4e once again shows details concerning the movement kinematics of the pivoting and/or lifting device 21. Hereby, the attachment condition is shown in the upper hatched position (see FIG. 2a or FIG. 3a, at the left in each case), and the cleaning condition is shown in the lower hatched position (see FIG. 2a to FIG. 3a, in each case the right position). The adapter 2 is not shown here for purposes of clarification. Once again, one can clearly see here that in the attachment position, a simple frontal accessibility by an operating person is possible due to the perpendicular position, and in the cleaning condition a good alignment to a flat trough base is possible. It is evident from the kinematics that it is hereby the case of pivoting and lifting kinematics. By way of this, one succeeds in the pivot radius being kept relatively small and thus a best possible spatial utilisation being achieved, i.e. the necessary volume in the ultrasound bath being able to be kept small, by which means an even more efficient subjection to ultrasound is possible.

Figure 4E:
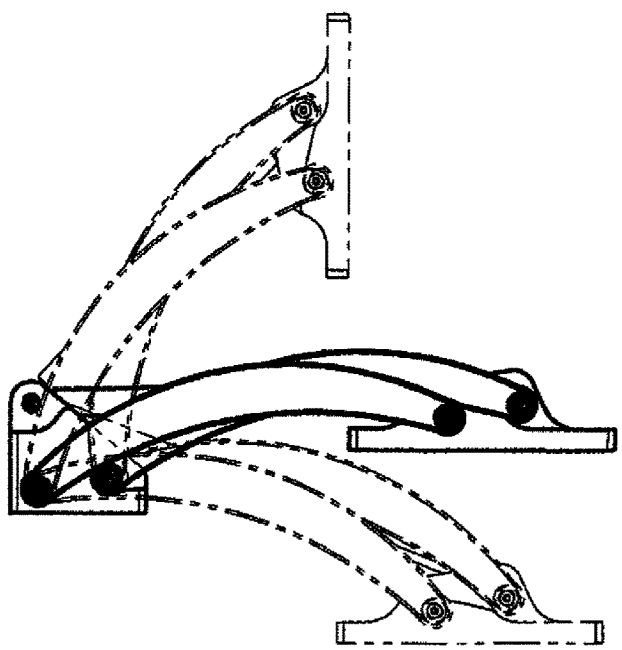
Figure 4D:
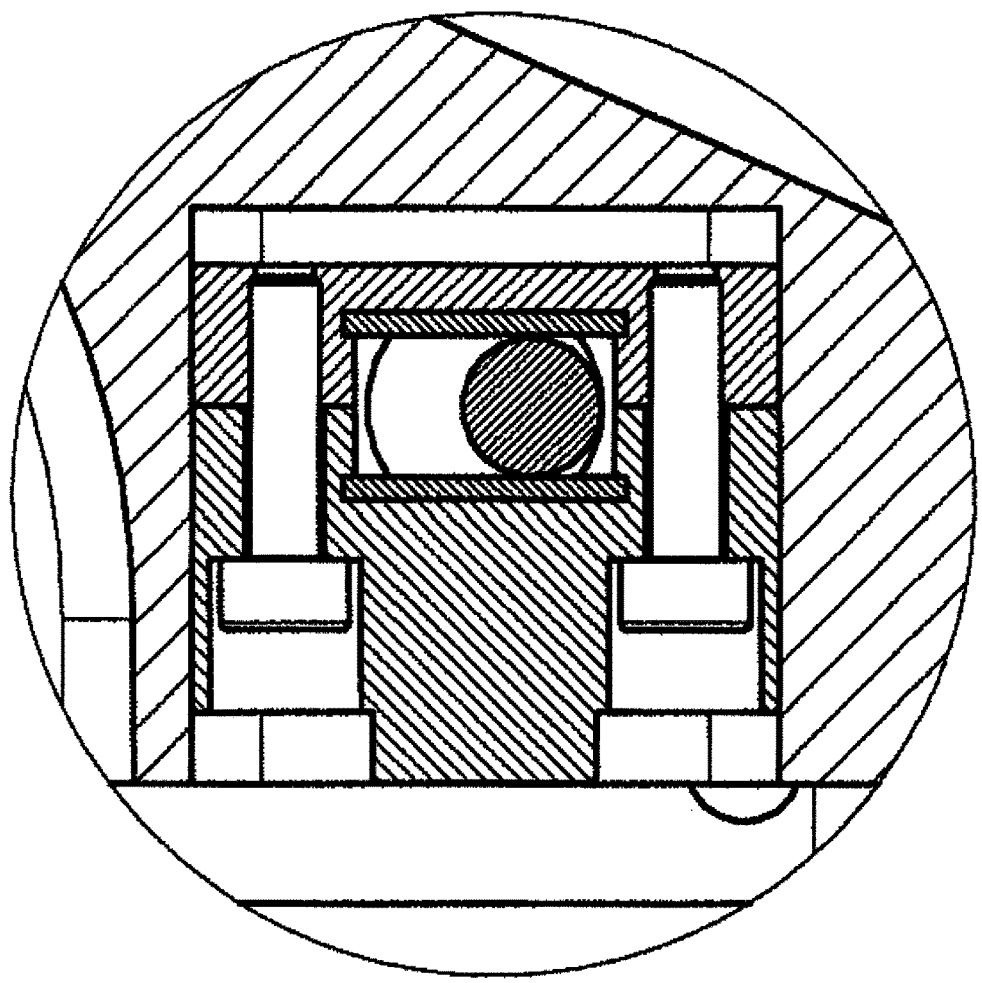
Figure 4H:
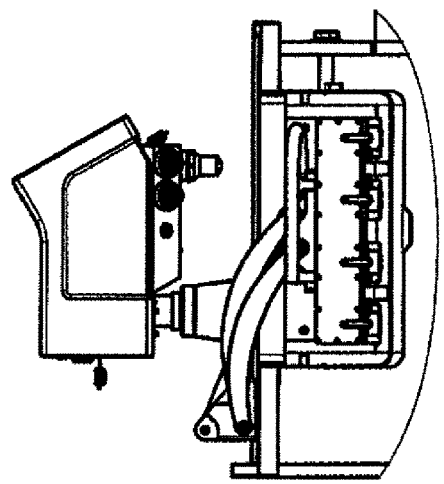
Figure 4G:
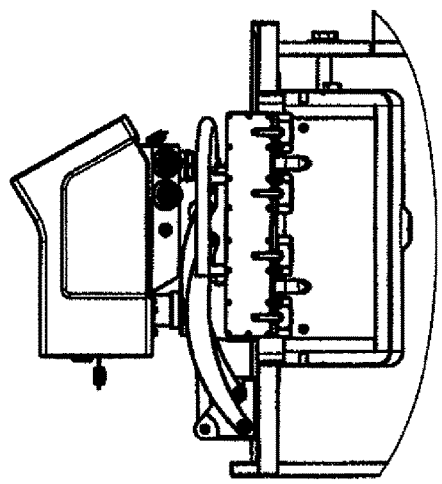
Figure 4F:
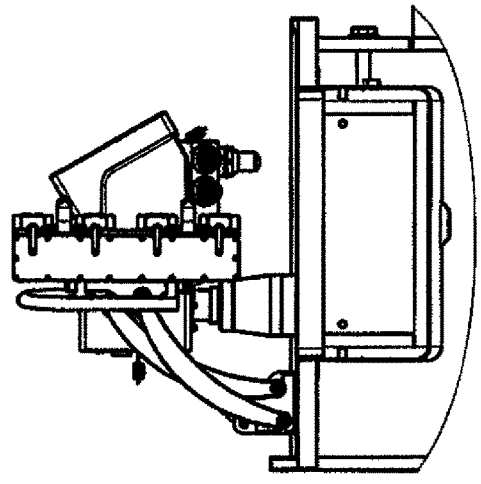

The movement condition of the pivoting and lifting device 21 with a coupled-on adapter (the positions here correspond to the conditions represented in FIG. 4e) is shown once again with reference to the FIGS. 4f and 4g. In other words, aspects of this pivoting and lifting device 21 are dealt with once again:

A possibility of moving a box firstly linearly, and then, from a certain point, in a rotary manner should therefore be found due to the necessity of an optimal and simple handling and on account of the defined geometric conditions. This is implemented by a two-arm guidance, which is moreover assisted by a gas tension spring (or gas compression spring). The system moreover ensures a simple dismantling ability of the components and an implemented safety from incorrect operation.

The basic movement forms are firstly dealt with, and these are to be seen particularly well in the FIGS. 4e to 4h. If two equally long arms are given (see FIG. 4e), whose movement pivots are assembled on both sides in their mounting parts, parallel and at the same distance to one another, then these mounting parts move to one another either in a parallel or rotatory manner, depending on their position. In the position, in which all four pivots are located on a line, the movement can go from one into the other form (see FIG. 4e). The arms are now prevented from moving in the form which is not desired, by way of certain stops and obstacles. Moreover, an external force is provided, which forces the arms into the desired form of motion (i.e. the attachment condition or the cleaning condition). Under certain circumstances, a loading cannot be achieved over the longer term due to the geometric setting of the stops/obstacles, since a lapsing into the undesired movement form cannot be completely ruled out due to manufacturing tolerances and the elastic deformation of the parts. A clean movement of the arms in the desired form is rendered possible by way of an external force which constrains the arms into the desired movement form, in order to prevent a forced movement by the user into the form which is not desired.

The function of the gas compression spring/gas tension spring is briefly dealt with hereinafter.

A gas tension spring is moreover integrated in the described mechanism. This fulfills essentially two functions: (1) relief of load on the user when moving the arm as well as (2) constraining the arm into the desired movement form. The gas tension spring on account of its tension force and given a suitable assembly is loaded counter to the weight force of a load fastened to the mechanism. If the operating person wishes to move this load on the mechanism, then the gas compression spring acts in an assisting manner, so that the user does not need to counteract the complete weight force of the load. This can go as far as the load being moved on its own accord as a result of an impulse by the user. The gas tension spring, as described above, can moreover keep the arm in its movement pattern and also to a certain extent constrain the arm out of an undesired form into the desired pattern. Here the position of the axes of the springs on both mounting parts is to be taken account of. It needs to be matched to the spring force, the weight force of the load and the geometry of the mechanism.

With the envisaged part according to the figures, which are to be understood purely by way of example, a mirror-symmetrical construction with a centrally positioned gas tension spring and four arm parts has been selected. In each case, two of these arm parts lie on the same axes, in order to avoid the occurrence of forces and moments in the lateral direction. For this, the arm pairs are connected to one another such that they cannot rotate relative to their mounting shaft and thus to one another. A lateral rotation of the arm is therefore counteracted to a further extent. The geometry of the pivoting and/or lifting device 21 and in particular the positioning and the force of the gas tension spring/gas compression spring 22 have been selected such that a course of forces arises, with which the load holds this in the lowermost position (cleaning condition), and the load and the tension force of the gas compression spring compensate one another at mid-height, so that device 21 remains in this position without further external loading. If one moves the device 21 higher up, then the tension force is predominant, and the pivot mechanism is automatically moved into the attachment condition (uppermost position). The applied gas compression spring 22 is limited in speed, in order to avoid a loading of the device 21 and danger to the user.

As already mentioned above, the mounting shaft of the gas tension spring/gas compression spring is slightly crowned so that it does not experience any laterally acting movements, which in the worst case would lead to a leakage of the gas compression cylinder. The device 21 can be fixed to an operating table by way of rail-like fixation devices (see FIG. 1), and moreover different adapters 2 (likewise see FIG. 1) can be positioned on the device. It is envisaged that a disassembly of the holder is not possible if the device 21 is not located at its uppermost position (e.g. attachment position). To this end, at least one of the connection shafts of the arm parts comprises an eccentric part. A bolt runs on this, said bolt moving downwards and moving into a bore with the downward movement. The bolt blocks in the case that the user now wishes to pull the device 21 out of its holder or mounting. The blocking bore is located for example on a sheet metal part which is screwed into the holder part of the device 21. A cavity is located below the tongue of the sheet metal part with the blocking bore. If the user now presses the device 21 downwards without having pushed it on completely, so that the bolt cannot move into the bore, then the sheet metal tongue is pressed downwards and the device is not otherwise damaged.

The material selection for the device 21 is to be made in accordance with the requirements. The arm parts for example can consist of metal frames around which blue plastic is moulded. On the one hand the required stability is achieved by way of this and on the other a simple cleaning is rendered possible. The arm part is prevented from colliding with the edge of the trough of an ultrasound bath 8 (see FIG. 1) by way of the arched shape (see figures, which show this arched shape in the lateral view).

FIGS. 5a to 5c show details of a channel selector 25 which is applied in a system 1, in particular for application in a suction device and/or pressure device for rinsing a lumen of a medical instrument 3. The functioning manner of a corresponding channel selector, for which an independent protection is sought, is already dealt with in the introductory part of the description.

The invention, inter alia, relates to the following aspects:
1. A movement device (1), comprising
    an adapter (2) for coupling at least one medical instrument (3), wherein
    the adapter (2) comprises at least one coupling element (4) which is movable by way of a drive, wherein the coupling element is designed such that on coupling the medical appliance, at least one region of the medical appliance can be brought into movement by way of moving the coupling element, wherein
    the force transmission between the drive and the coupling element is effected in a contact-free manner.
2. A movement device according to aspect 1, characterised in that the coupling element (4) is designed in a rotatable manner.
3. A movement device according to one of the preceding aspects, characterised in that several coupling elements (4) are provided in an adapter.
4. A movement device according to one of the preceding aspects, characterised in that the contact-free force transmission device is designed as a magnetic coupling (5).
5. A movement device according to one of the preceding aspects, characterised in that a drive (6) and the coupling element (4) are separated from one another by way of a fluid-tight separating layer.
6. A movement device according to aspect 5, characterised in that the separating layer is designed as a plastic wall and/or as a plastic membrane.
7. A movement device according to one of the preceding aspects, characterised in that this is designed such that it can be placed in a water bath, an ultrasound bath (8), a water jet and/or in a water spray mist.
8. A movement device according to aspect 7, characterised in that the water bath can be subjected to ultrasound.
9. A movement device according to one of the preceding aspects, characterised in that the at least one medical instrument (3) is an endoscopic instrument with at least one moving part which is movable in accordance with a coupling element.
10. A movement device according to aspect 9, characterised in that the medical appliance (3) is designed as an endoscopic instrument with a coupling part (9) for coupling onto the adapter, with an instrument shank (10) connecting onto the coupling part and with an operation part (11) attached on the end of the instrument shank which is away from the coupling part.
11. A movement device according to aspect 10, characterised in that several operation parts (11) which are movable independently of one another and which are movable independently of one another by different coupling elements (4) are provided.
12. A movement device according to one of the preceding aspects, characterised in that a drive-side part of the force transmission comprises a rotatable drive element (12) which preferably comprises permanent-magnetic material (13) at least in regions and is preferably axially displaceable with respect to other parts of the drive.
13. A movement device according to one of the preceding aspects, characterised in that a driven-side part of the force transmission is provided, in which part the coupling element (4) is resiliently mounted.
14. A movement device according to one of the preceding aspects, characterised in that with regard to the driven-side part of the force transmission, a compression spring (14) is arranged between the coupling element (4) and a rotatable driven element (15), wherein the movement element at least in regions comprises permanent-magnetic material (16).
15. A movement device according to one of the preceding aspects, characterised in that a drive side part and a driven-side part of the force transmission device each comprises at least one region of permanent-magnetic material (13, 16), and these regions are in relation to one another such that a rotation of the drive-side part results in a rotation of the driven-side part.
16. A movement device according to aspect 15, characterised in that in each case 1-16 permanent magnets are provided at the drive side and/or the driven side.
17. A movement device according to one of the preceding aspects, characterised in that one motor is provided per coupling element (4).
18. A movement device according to aspect 17, characterised in that the individual motors are movable independently of one another.

19. A movement device according to one of the preceding aspects, characterised in that the drive provides at least one electronic and/or mechanical torque limitation, which is designed in a manner such that the torque which is exerted by the coupling element (4) onto a mechanism (18) of the medical instrument can be limited.
20. A movement device according to one of the preceding aspects, characterised in that a suction rinsing and/or pressure rinsing device is provided for rinsing at least one lumen (19) of a medical appliance.
21. A movement device according to one of the preceding aspects, characterised in that a control unit (20) is provided for the control of the drive and/or of a rinsing device and/or of an ultrasound device.
22. A movement device according to one of the preceding aspects, characterised in that several medical instruments (3) can be coupled in an adapter (2).
23. A movement device according to one of the preceding aspects, characterised in that different adapters (2) can be integrated into the movement device and/or exchanged amongst one another.
24. A system, comprising a movement device according to one of the preceding aspects, as well as an ultrasound bath (8), wherein the system is designed such that medical instruments (3) which are coupled onto the movement device, at least in regions can be arranged within the ultrasound bath (8), preferably below a water surface of the ultrasound bath.
25. A system for cleaning medical instruments (3), comprising a movement device with
    an adapter (2) for coupling at least one medical instrument (3), wherein
    the adapter (2) comprises at least one coupling element (4) which is movable by way of a drive, wherein the coupling element (4) is designed such that on coupling the medical instrument (3), at least a region of the medical instrument (3) can be brought into movement by way of movement of the coupling element (4),
    moreover comprising a pivoting and/or lifting device (21), which is designed in a manner such that the adapter (2) is displaceable between
    a) an attachment condition which is arranged above the trough bath (see FIG. 2A, left) and
    b) a cleaning condition, in which the adapter at least in regions is arranged below a water surface (see FIG. 2A, right).
26. A system according to aspect 25, characterised in that difference adapters (2) can be coupled onto the pivoting and/or lifting device (21).
27. A system according to one of the aspects 25 ff, characterised in that a rotation of the coupled-on adapter is effected between the attachment condition and the cleaning condition, on account of the construction type of the pivoting and/or lifting device.
28. A system according to one of the aspects 25ff, characterised in that the pivoting and/or lifting device (21) can be locked in at least one position.
29. A system according to one of aspects 25ff, characterised in that in the attachment condition, medical instruments (3) can be coupled on frontally, seen from a standing operating person.
30. A system according to one of the aspects 24ff, characterised in that in the cleaning condition, medical instruments (3) can be arranged essentially parallel to the base of a trough of an ultrasound bath (8).
31. A system according to one of the aspects 24ff, characterised in that in the cleaning condition, medical instruments (3) are arranged in a manner such that no further components are present between the base and/or walls of the trough, as well as the medical instruments.

LIST OF REFERENCE NUMERALS 1 movement device
2 adapter
3 medical instrument
4 coupling element
5 magnetic coupling
6 drive
7 plastic wall
8 ultrasound bath
9 coupling part
10 instrument shank
11 operation part
12 rotatable drive element
13 permanent-magnetic material (drive-side)
14 compression spring
15 rotatable driven element
16 permanent-magnetic material (driven side)
17 motor
18 mechanism of the medical instrument
19 lumen for the suction and/or pressure rinsing of the medical instrument
20 control unit
21 pivoting and/or lifting device
22 gas compression spring (=gas tension spring)
23 detent mechanism
24 separating layer
25 channel selector

The invention claimed is:
1. A movement device, comprising
    an adapter for coupling to at least one medical instrument,
    the adapter including at least one coupling element which is movable by way of a drive, the coupling element being designed such that on coupling the at least one medical instrument, at least one region of the at least one medical instrument is brought into movement by way of moving the coupling element,
    a force transmission device between the drive and the coupling element being effected in a contact-free manner,
    several coupling elements being provided in the adapter,
    the at least one medical instrument being an endoscopic instrument with at least one moving part which is movable in accordance with the coupling element,
    the at least one medical instrument being the endoscopic instrument having a coupling part for coupling onto the adapter, with an instrument shank connecting onto the coupling part and with an operation part attached on an end of the instrument shank which is away from the coupling part, and several operation parts which are movable independently of one another being movable independently of one another by different coupling elements,
    one motor being provided per coupling element.
2. The movement device according to claim 1, wherein the force transmission device is a magnetic coupling.
3. The movement device according to claim 1, wherein the drive and the coupling element are separated from one another by a fluid-tight separating layer.
4. The movement device according to claim 1, wherein a drive-side part of the force transmission device includes a rotatable drive element which has permanent-magnetic material at least in regions and is axially displaceable with respect to other parts of the drive.

5. The movement device according to claim 1, wherein a driven-side part of the force transmission device is provided in which the coupling element is resiliently mounted.

6. The movement device according to claim 5, wherein with regard to the driven-side part of the force transmission device, a compression spring is arranged between the coupling element and a rotatable driven element.

7. The movement device according to claim 1, wherein a drive-side part and a driven-side part of the force transmission device each includes at least one region of permanent-magnetic material, and the at least one region are in relation to one another such that a rotation of the drive-side part results in a rotation of the driven-side part.

8. The movement device according to claim 1, wherein the drive provides at least one of at least one electronic and at least one mechanical torque limitation which is designed in a manner such that the torque which is exerted by the coupling element onto a mechanism of the at least one medical instrument is limited.

9. The movement device according to claim 1, wherein at least one of a suction rinsing and a pressure rinsing device is provided for rinsing at least one lumen of the at least one medical instrument.

10. A system comprising the movement device according claim 1 as well as an ultrasound bath, wherein the system is designed such that medical instruments which are coupled onto the movement device at least in regions is arranged within the ultrasound bath, below a water surface of the ultrasound bath.

11. A system for cleaning medical instruments according to claim 1,
further comprising at least one of a pivoting and a lifting device, which is designed in a manner such that the adapter is displaceable between
a) an attachment condition which is arranged above a trough bath and
b) a cleaning condition, in which the adapter at least in regions is arranged below a water surface.

\* \* \* \* \*